(12) United States Patent
Chang et al.

(10) Patent No.: US 6,178,825 B1
(45) Date of Patent: Jan. 30, 2001

(54) HONEYCOMB SHEAR TESTING METHOD

(75) Inventors: Dick J. Chang, Los Angeles; Pierre R. Valenzuela, Pico Rivera; Richard P. Welle, Huntington Beach, all of CA (US)

(73) Assignee: The Aerospace Corporation, El Segundo, CA (US)

( * ) Notice: Under 35 U.S.C. 154(b), the term of this patent shall be extended for 0 days.

(21) Appl. No.: 09/340,515

(22) Filed: Jun. 28, 1999

(51) Int. Cl.[7] ............................................. G01N 3/24
(52) U.S. Cl. ............................................. 73/846
(58) Field of Search ............................. 73/841, 818, 826, 73/846, 856

(56) References Cited

U.S. PATENT DOCUMENTS

| | | | |
|---|---|---|---|
| 5,237,860 | * | 8/1993 | Kato et al. .............................. 73/105 |
| 5,275,489 | * | 1/1994 | Borneman et al. .................. 374/153 |
| 5,315,861 | * | 5/1994 | Egan et al. ............................... 73/37 |
| 5,913,242 | * | 6/1999 | Stussi ................................ 73/379.04 |

* cited by examiner

Primary Examiner—Max Noori
(74) Attorney, Agent, or Firm—Derrick Michael Reid

(57) ABSTRACT

A shear test fixture and method determines the shear strength of a honeycomb having elongated cells extending between two ends filled with a filler material with a load applied to one end relative to the other end introducing shear stress without introducing compression or tension stress for improved shear strength testing.

18 Claims, 2 Drawing Sheets

SHEAR TESTING APPARATUS

SHEAR TESTING APPARATUS

SHEAR TESTING ASSEMBLY

HONEYCOMB SHEAR TESTING METHOD

STATEMENT OF GOVERNMENT INTEREST

The invention was made with Government support under contract No. F04701-93-C-0094 by the Department of the Air Force. The Government has certain rights in the invention.

FIELD OF THE INVENTION

The invention relates to the field of material testing. More particularly the present invention relates to the testing of the mechanical properties of composite materials, such as honeycomb composites.

BACKGROUND OF THE INVENTION

Honeycomb structures have been used in many structural applications. Honeycombs have been widely used in both aircraft and aerospace industries to reduce weight while maintaining mechanical strength. For example, honeycombs are used in cargo floors in commercial aircraft, are used as skin panels of military aircraft wings, are used in payload shrouds on space launch vehicles and are used as optical structures in spacecraft systems. Honeycomb structures are also used as energy absorbers such as barriers in automobile crash tests. The energy absorption is based on the work done through elastic buckling, plastic yielding, and brittle crushing of the cell walls.

In analytical modeling, such as finite element analysis (FEA), honeycomb structures are generally assumed to be orthotopic. Material properties such Young's moduli, shear moduli, and Poisson's ratio, and inelastic characteristics, yield strength, and the failure strength or strain are needed as input for these models. All the mechanical property information must be accurately determined and provided as input for the computer codes before any reasonable prediction can be obtained using the codes.

At the present time, only limited material property information for honeycomb is available. Such data as is available is primarily simple compression data because compression testing is simple and easy to implement. Very little data is available for shear or tension loading, in particular, at high strain rates. When shear or tension data are available, they are limited to modulus measurements in the elastic range, or to incipient yielding. At higher tension or shear loads, the honeycomb separates at the bonding interface with the face sheet, making it impossible to determine the tension and shear properties of the honeycomb structure itself. Thus it is difficult to address the overall constituent behavior of honeycomb structures. For completely assessing the failure of a honeycomb structure, data from simple tension, simple compression, simple shear, and various combined stress fields are needed. The fact that little of the needed data is available for analytical prediction has established a high need to generate these data experimentally.

Hexcel Corporation has long provided data on honeycomb structures. An exemplar configuration of an aluminum honeycomb, designated as 1/4-5052-0.004-7.9, has a cell size of 0.25 inches, is made from 5052 aluminum, has a wall thickness of 0.004 inches and a density 7.9 lb per cubic foot. The width direction shear strength data of this Hexcel honeycomb ranges from 390 to 440 psi. The tension shear or compression shear is what has been used to determine the shear strength. This data has limitations, in that the data book indicates that the honeycomb is not being subjected to pure shear but to a combination of shear and tension/compression. The tensional compression component varies with core thickness so that thicker cores will have a lower apparent shear strength than thinner cores. This method of testing does not generate valid shear mechanical properties yet this method for testing honeycomb specimens has been used for more than 40 years. Accurate shear failure data are needed in establishing failure criteria. Currently there is no test method existing to conduct a full range of valid shear-strain tests on core material up to failure. These and other disadvantages are solved or reduced using the invention.

SUMMARY OF THE INVENTION

An object of the invention is to provide a test method for determining the mechanical properties of honeycomb materials.

Another object of the invention is to provide a test method for determining the shear properties of honeycomb materials.

The invention is directed to a testing method to determine mechanical shear properties including shear failure strength of a honeycomb specimen. An improved test fixture is used to place a honeycomb specimen under shear without tension or compression loading so as to obtain valid shear mechanical properties. A filler material is injected under partial vacuum pressure into the ends of the cells of a honeycomb specimen, and the ends are then fastened to opposing fixture-fastening means. A load is then applied to one end to place the honeycomb specimen in shear without introducing tension or compression forces upon the honeycomb specimen. The testing method applies to any two opposite faces of a cubic honeycomb specimen. The testing method works on all three principal directions. Using vacuum injection of filler material, the test method is applied to the two opposite faces whose normal is parallel to the honeycomb cell. When conducting the same test in the two other directions, the potting operation is much simpler and no partial vacuum is necessary. The test method produces consistent reliable mechanical property data for the honeycomb specimen. These and other advantages will become more apparent from the following detailed description of the preferred embodiment.

DETAILED DESCRIPTION OF THE PREFERRED EMBODIMENT

Figure 1:
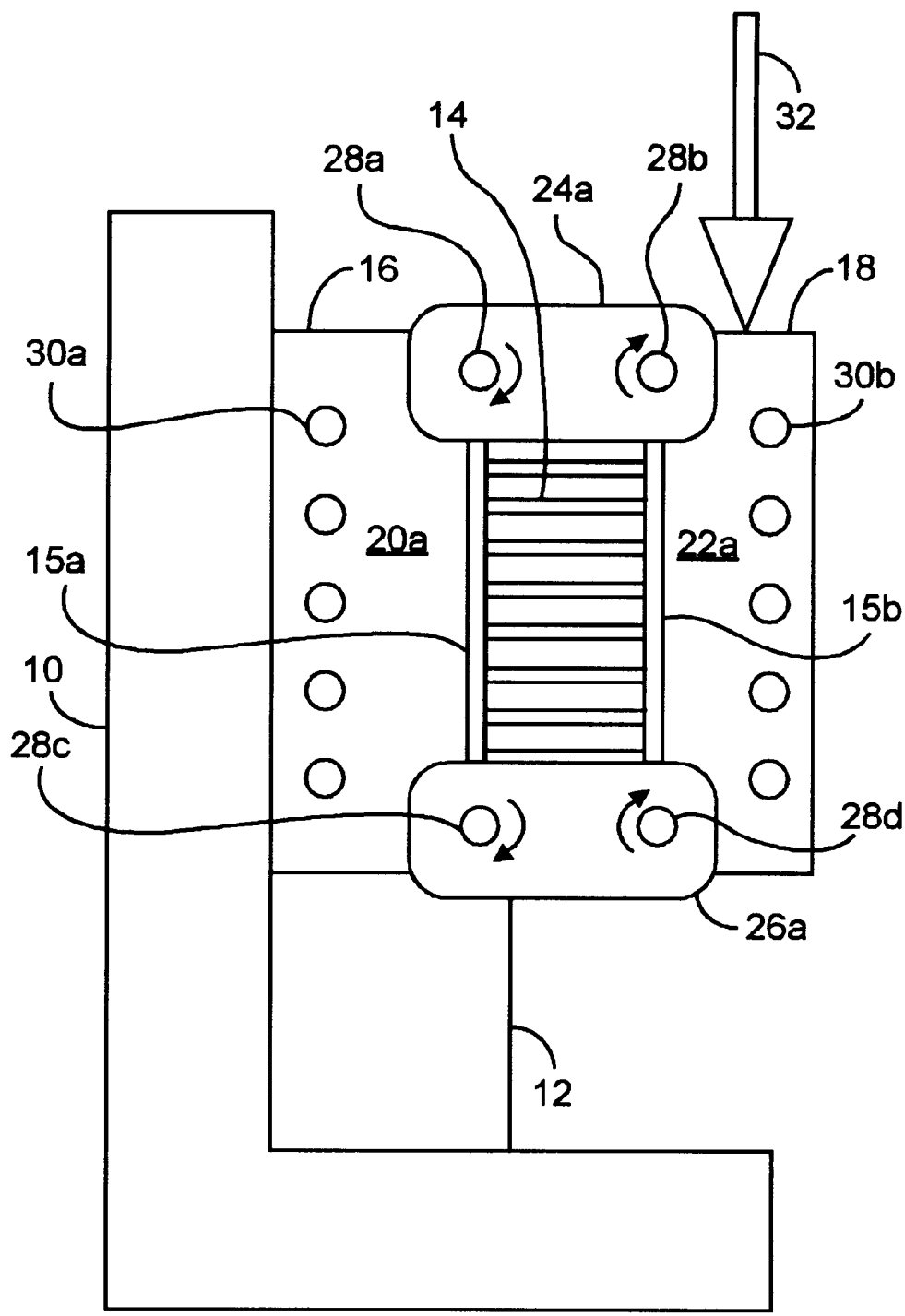
FIG. 1 is a frontal view of a shear testing apparatus.
Figure 2:
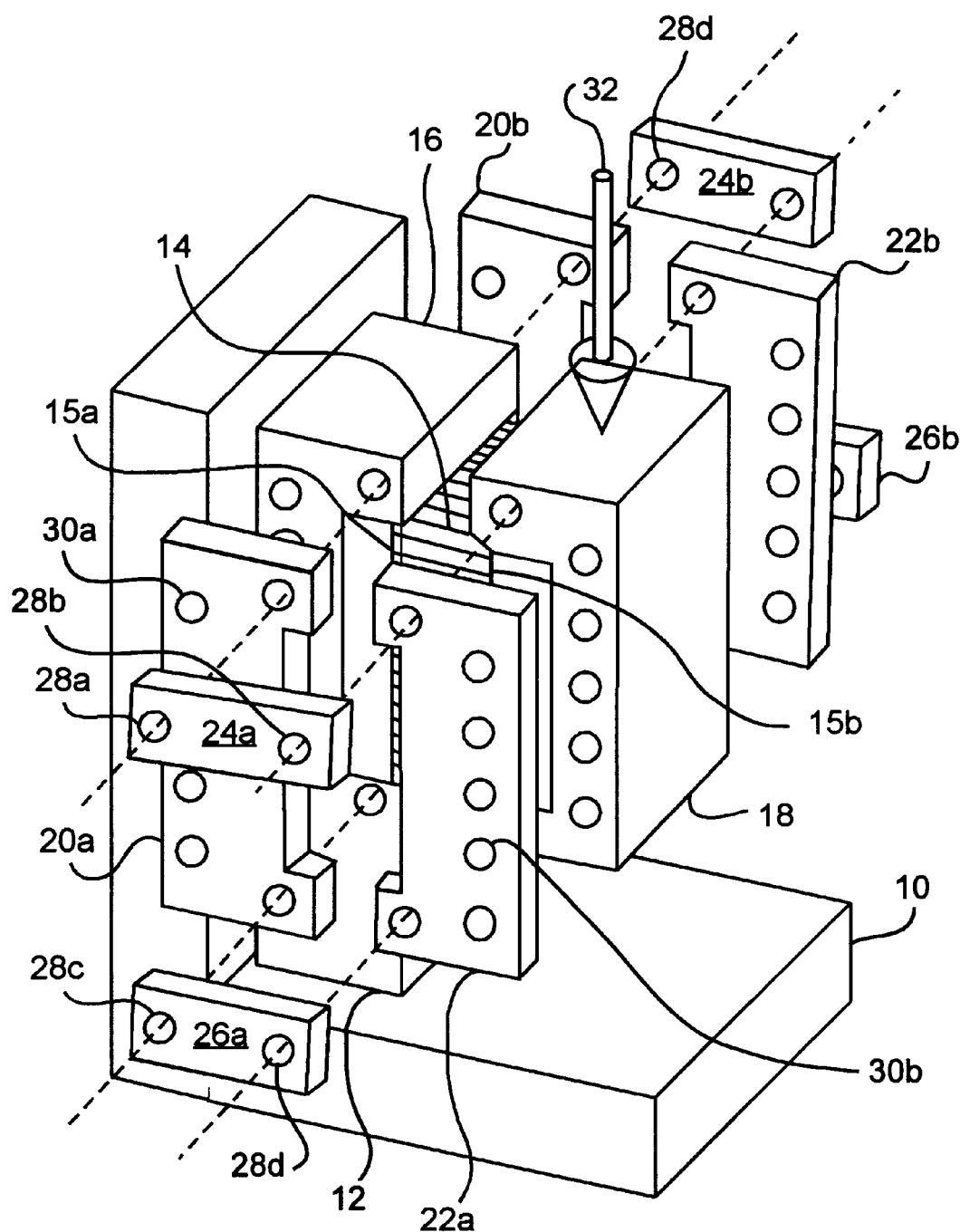
FIG. 2 is an assembly drawing of the shear testing apparatus.

An embodiment of the invention is described with reference to the Figures using reference designations as shown in the Figures. Referring to the Figures, the shear test fixture includes a right angle shaped base 10 having a supporting block 12 for supporting a cubic honeycomb 14. The honeycomb 14 contains cells shown as horizontal lines having opposing ends 15a and 15b filled with a filler potting material. The honeycomb 14 is disposed in opposing clamps 16 and 18. Front and back left vertical plates 20a and 20b are respectively secured to frontal and back sides of the clamp 16, as shown, and front and rear right vertical plates 22a and 22b are respectively secured to front and rear sides of clamp 18, as shown. Front top horizontal link 24a is attached horizontally between the tops of the front plates 20a and 22a. Front bottom horizontal link 26a is attached horizontally between the bottoms of the front plates 20a and 22a.

Back top horizontal link 24b is attached horizontally between the tops of the back plates 20b and 22b. Back bottom horizontal link 26b is attached horizontally between the bottoms of the back plates 20b and 22b. Top and bottom horizontal links 24ab, and 26ab are respectively secured to left and right vertical plates 20ab, and 22ab using mounting holes 28ab and 28cd, only one of each is designated as such with mounting pins not shown for clarity. The left and right vertical plates 20ab, and 22ab, are respectively secured to the clamps 16 and 18 using left and right mounting holes 30a and 30b, only one each is designated as such with mounting pins not shown for clarity. In operation, a load 32 is applied to the right clamp 18 to generate shear stress to the honeycomb 14. As the load 32 increases, horizontal brackets 24a and 24b, and 26a and 26b rotate about holes 28a and 28b, with the left clamp 16 remaining stationary while right clamp 18 moves downward. The honeycomb 14 is thereby deformed in the shear mode within the fixture. This condition continues until a shear failure occurs. Simultaneous measurement of the load and the associated strain allow construction of a complete shear stress-strain curve.

The preferred cellular structure 14 is a honeycomb constructed with hexagonal cells. However, any honeycomb or any other cellular structure may be used. The honeycomb may be made of aluminum material having a wall thickness of the cells of 0.05 inches, having center-to-center distances of 0.36 inches in the elongated direction, and having 0.25 inches in the short (Y) direction. The nominal size of the honeycomb specimen is two inches by two inches by two inches. To make the specimen suitable for shear testing, the two ends 15a and 15b are made rigid for secure holding in the test fixture. The ends 15a and 15b are made rigid by potting part of the specimen using soft potting or filler material. The filler material preferably would not cause significant stress concentrations in the cell material. A polymer epoxy material with low viscosity may be used for this application because polymer epoxy material is nearly incompressible. It has low modulus and yet becomes very rigid when constrained for deforming. An exemplar epoxy used in potting may be Master Bond 31, a two-part polymer system, which has a density of 1.23 gm/cc and viscosity of 2000 to 3000 cP at 75 xF before curing. In addition, this epoxy has very low out-gassing characteristics. Out-gassing must be avoided because it can generate high pressures inside the cells, forcing the filler material out of the cell during cure.

The potting operation is done in two stages. First, the end 15a of the honeycomb is dipped approximately 0.5 inches deep into the uncured polymer. After an overnight cure, the second opposing end is ready to be potted. The second stage potting required a partial vacuum to reduce the pressure inside the cell so that the polymer can reach the predetermined penetration depth after the potting. After potting the first end 15a, the cells have only one end open, the second end 15b. If the second stage potting is done at ambient pressure, there will be very little epoxy penetration into the cell because air in the cell cannot be vented. If the specimen is dipped into the epoxy under a partial vacuum, followed by bringing the pressure up to ambient, then the epoxy will penetrate into the cell at a depth such that the cell pressure would increase to ambient pressure. For example, a specimen of 2 inches height is first potted on one end to a depth of 0.5 inches with epoxy. In order to have a 0.5 inches deep epoxy on the other end, the sample is suspended with the open end down over an uncured epoxy bath in a vacuum chamber. The chamber is sealed and the pressure is reduced to a few torr to remove dissolved gases from the epoxy. The pressure is then increased to 506 torr. The specimen is then lowered into the bath and the pressure in the chamber is returned to one atmosphere. The increasing pressure causes the epoxy in the bath to penetrate into the open cells to a depth of 0.5 inches.

The testing fixture consisted of two clamps 16 and 18, four vertical metal plates 20ab and 22ab and four linkage bars. Each of the clamps 16 and 18 is machined to have a recess to receive the potted end portion 15a and 15b of the specimen 14. The four links 24ab and 26ab are secured using dowel pins, not shown, in holes 30ab. The holes are aligned vertically with the potting edges of the specimen 15ab so that their center-to-center distance represents the gauge length of the specimen 14. The links 24ab and 26ab also served to react the tension through the upper links 24ab and compression through the lower links 26ab through rotation as shown induced by the vertically applied load 32. The net result is that only shear load is resisted by the honeycomb specimen 14. The gauge length area of the entire honeycomb specimen is deformed under the load 32 into a parallelogram shape representing shear deformation.

The specimen 14 is mounted into the fixture. The clamp 16 is fastened to the heavy support 10 while the other plate 18 is loaded externally by the load 32. The external loading source 32 can be a loading machine or an impactor, not shown. The loading may be, for example, a Riehle loading fixture at a displacement rate of approximately 10.0 inches/min.

An improvement is that the specimen 14 is rigidized at both ends 15a and 15b by the use of polymer epoxy so that it can be gripped firmly at the ends by the clamps 16 and 18. The introduction of low modulus polymer material will not cause high stress concentration in the aluminum at the end of the potting material. The near incompressibility of polymer material makes the ends rigid because it is encapsulated inside the honeycomb cells. Another improvement is that the fixture design allows only shear load to be transferred into the specimen with the applied load-induced moment taken away by the upper and lower linkage bars.

The invention can be applied to any cellular structure such as honeycomb having elongated cells. Those skilled in the art can make enhancements, improvements and modifications to the invention, and these enhancements, improvements and modifications may nonetheless fall within the spirit and scope of the following claims.

What is claimed is:

1. A method of inducing stresses in a structure of cells positioned at a first end and at a second end of the structure, the method comprising the steps of, disposing a filler material into the cells at the first end and into the cells at the second end of the structure, rigidly clamping the first end of the structure, rigidly clamping the second end of the structure for transferring a load force upon the structure, and applying load induced displacement to the second end relative to the first end, the load inducing stresses in the structure.

2. The method of claim 1 wherein the load is a rotational load inducing shear and normal stresses in the structure.

3. The method of claim 1 wherein the load is a compression load inducing compressive stresses in the structure.

4. The method of claim 1 wherein the load is a pulling load inducing tension stresses in the structure.

5. The method of claim 1 further comprising the step of, determining the mechanical properties of the structure under the load.

6. The method of claim 1 wherein the load is a shear load, the method further comprising the step of, determining the shear properties of the structure under the shear load.

7. The method of claim 1, wherein the disposing step comprises the steps of, disposing the filler material into the first end of the cells, creating a partial vacuum within the cells at the second end, and vacuum filling the second end of the structure with the filler material.

8. A method of testing for shear properties of a structure of cells positioned at a first end and at a second end of the structure, the method comprising the steps of, disposing a filler material into the cells at the first end and into the cells at the second end of the structure, rigidly clamping the first end of the structure, rigidly clamping the second end of the structure for transferring a load force upon the structure, applying load induced displacement to the second end relative to the first end, the load inducing stresses in the structure, and determining the shear properties of the structure upon deformation the structure when under the load.

9. The method of claim 8 wherein the deformation of th e structure is elastic deformation.

10. The method of claim 8 wherein the deformation of the structure is inelastic deformation.

11. The method of claim 8 wherein the shear properties comprises shear failure strength.

12. The method of claim 8 wherein the shear properties comprises shear yield strength.

13. The method of claim 8, wherein, the structure is a honeycomb structure, and the cells are elongated hexagonal cells extending from the first end to the second end.

14. The method of claim 8 wherein the filler material is a polymer epoxy material with low viscosity, the method further comprising the step of curing the polymer epoxy material until rigid in the first end and the second end.

15. The method of claim 8 wherein the load is applied at a predetermined rate distance per minute.

16. The method of claim 8, wherein the disposing step comprises the steps of, disposing the filler material into cells at the first end, creating a partial vacuum within the cells at the second end, and vacuum filling the cells at the second end with the filler material.

17. A method of testing for shear properties of a honeycomb structure of elongated hexagonal cells extending between a first end and a second end of the honeycomb structure, the method comprising the steps of, disposing a filler material into the elongated hex cells at the first end, creating a partial vacuum within the elongated hexagonal cells, vacuum filling the elongated hexagonal cells at the second end with the filler material, rigidly clamping the first end of the honeycomb structure, rigidly clamping the second end of the honeycomb structure for transferring a load force upon the honeycomb structure, applying load induced displacement to the second end relative to the first end, the load inducing stresses in the entire honeycomb, and determining the shear properties of the honeycomb structure upon deformation of the honeycomb structure when the load is applied.

18. The method of claim 17 wherein the filler material is a polymer epoxy material with low viscosity, the method further comprising the step of curing the polymer epoxy material until rigid.

* * * * *